US010568502B2

(12) United States Patent
Leung et al.

(10) Patent No.: US 10,568,502 B2
(45) Date of Patent: Feb. 25, 2020

(54) VISUAL DISABILITY DETECTION SYSTEM USING VIRTUAL REALITY

(71) Applicant: The Chinese University of Hong Kong, Shatin, N.T., Hong Kong (CN)

(72) Inventors: Kai Shun Christopher Leung, Hong Kong (CN); Ka Ngai Alexander Lam, Hong Kong (CN); Yuen Ying Elaine To, Hong Kong (CN)

(73) Assignee: The Chinese University of Hong Kong, Shatin, N.T., Hong Kong (CN)

( * ) Notice: Subject to any disclaimer, the term of this patent is extended or adjusted under 35 U.S.C. 154(b) by 84 days.

(21) Appl. No.: 15/466,348

(22) Filed: Mar. 22, 2017

(65) Prior Publication Data

US 2017/0273552 A1    Sep. 28, 2017

Related U.S. Application Data

(60) Provisional application No. 62/312,096, filed on Mar. 23, 2016.

(51) Int. Cl.
*A61B 3/02* (2006.01)
*A61B 3/00* (2006.01)
*H04N 13/144* (2018.01)
*H04N 13/344* (2018.01)
*H04N 13/366* (2018.01)

(52) U.S. Cl.
CPC ............... *A61B 3/02* (2013.01); *A61B 3/005* (2013.01); *H04N 13/144* (2018.05); *H04N 13/344* (2018.05); *H04N 13/366* (2018.05)

(58) Field of Classification Search
None
See application file for complete search history.

(56) References Cited

U.S. PATENT DOCUMENTS

| | | | |
|---|---|---|---|
| 5,641,288 A | 6/1997 | Zaenglein | |
| 5,737,060 A | 4/1998 | Kasha, Jr. | |
| 6,184,847 B1 | 2/2001 | Fateh et al. | |
| 6,386,706 B1 | 5/2002 | McClure et al. | |
| 6,592,222 B2 | 7/2003 | Massengill et al. | |
| 7,033,025 B2 | 4/2006 | Winterbotham | |
| 8,047,652 B1 | 11/2011 | Collazo | |
| D701,206 S | 3/2014 | Luckey et al. | |

(Continued)

OTHER PUBLICATIONS

Chauhan, et al., "Practical recommendations for measuring rates of visual field change in glaucoma," Br J Ophthalmol. 2008;92:569-73.

(Continued)

*Primary Examiner* — Vu Nguyen
(74) *Attorney, Agent, or Firm* — Kilpatrick Townsend & Stockton LLP

(57) ABSTRACT

Techniques for a visual disability detection system that employs virtual reality to assess visual performance of a patient based on activities of daily living are described. The virtual reality platform can integrate the testing of different components of visual function based on activities of daily living to provide a direct and clinically relevant measure of the impact of any visual disability on a patient's daily life. By simulating daily tasks for evaluation of visual disability, clinicians can better understand from a patient's perspective how visual impairment affects their daily tasks and quality of life.

16 Claims, 10 Drawing Sheets

(56) References Cited

U.S. PATENT DOCUMENTS

| | | | |
|---|---|---|---|
| 8,957,835 B2 | 2/2015 | Hoellwarth | |
| 2012/0108909 A1* | 5/2012 | Slobounov | A61B 5/1124 600/300 |
| 2016/0007849 A1* | 1/2016 | Krueger | A61B 3/113 600/301 |
| 2017/0103571 A1* | 4/2017 | Beaurepaire | G01C 21/3667 |
| 2017/0148214 A1* | 5/2017 | Muniz-Simas | G06F 3/011 |
| 2017/0262049 A1* | 9/2017 | Kim | G06F 3/012 |

OTHER PUBLICATIONS

Jampel, "Glaucoma patients' assessment of their visual function and quality of life," Trans Am Ophthalmol Soc. 2001;99:301-317.

Mckean-Cowdin, et al., "Los Angeles Latino Eye Study Group. Severity of visual field loss and health-related quality of life," Am J Ophthalmol. 2007;143:1013-23.

Medeiros, et al., "Longitudinal changes in quality of life and rates of progressive visual field loss in glaucoma patients," Ophthalmology. 2015;122:293-301.

Patino, et al., "Los Angeles Latino Eye Study Group. The impact of change in visual field on health-related quality of life the Los Angeles Latino Eye Study," Ophthalmology. 2011;118:1310-7.

Qiu, et al., "Association between visual field defects and quality of life in the United States," Ophthalmology. 2014;121:733-40.

* cited by examiner

VISUAL DISABILITY DETECTION SYSTEM USING VIRTUAL REALITY

CROSS-REFERENCES TO RELATED APPLICATIONS

The present application claims priority to U.S. Provisional Application No. 62/312,096, filed on Mar. 23, 2016, which is herein incorporated by reference in its entirety for all purposes.

BACKGROUND

Assessment of the impact of visual performance on the activities of daily living in clinical medicine has been challenging. Evaluation of visual function in clinical practice has been largely predicated on visual acuity and visual field testing. There are other functional indicators including contrast sensitivity, color vision, and stereopsis which may influence visual performance, but these functional indicators are not routinely tested. Furthermore, how visual acuity and visual field and other visual performance indicators translate to visual disability impairing the activities of daily living is unknown. No objective clinical tests are currently available to evaluate visual performance directly related to patients' activities of daily living.

Patients with visual disability have difficulties in completing daily tasks (e.g. navigating in a street, walking down a flight of stairs, locating an object of interest, etc.). In some patients, the peripheral vision is significantly impaired although the central vision remains intact. In others, vision at night can be significantly impaired despite relatively normal vision at day time.

Embodiments of the present invention address these and other problems, individually and collectively.

BRIEF SUMMARY

Embodiments of the present invention provide techniques for a visual disability detection system that employs virtual reality to assess visual performance of a patient based on activities of daily living. Embodiments of the present invention is designed to evaluate and measure the performance of a person in completing daily tasks in different VR environments with different brightness and contrast levels, simulating activities of daily living in a variety of light conditions. Performance data such as the time required in completing a task, the number of collisions with the VR objects in the VR environments, the angle and the speed of collision, the size, color and contrast levels of the collided VR objects, etc. are recorded to compute performance scores. The performance scores can then be used to quantify the visual performance for assessment, grading and monitoring of visual disability of a person.

The virtual reality (VR) platform can integrate the testing of different components of visual function (e.g., visual acuity, visual field, contrast sensitivity, color vision, stereopsis, etc.), providing a new paradigm to measure and monitor visual disability in a variety of ocular and neurological disorders. Visual performance assessment based on activities of daily living can provide a direct and clinically relevant measure of the impact of any visual disability on a patient's daily life. By simulating daily tasks for evaluation of visual disability, clinicians can better understand from a patient's perspective how visual impairment affects their daily tasks and quality of life. This allows better clinical management of a variety of ocular diseases.

According to some embodiments, a process for visual disability detection may include generating a virtual reality simulation in a virtual reality environment with virtual reality objects, in which the virtual reality simulation simulates a real life activity that tests visual responses of the user. A system to run the process may include a visual disability detection system having a head-mounted display device, a sensor system communicatively coupled to head-mounted display device, and a computing device with processor communicatively coupled to the sensor system and the display. The process may further include displaying the virtual reality simulation on a head-mounted display, and monitoring voluntary and involuntary responses of the user via a sensor system during the virtual reality simulation. Visual performance scores can be computed based on the voluntary and the involuntary responses of the user to the virtual reality simulation, and visual disability metrics of the user can be determined based on the performance scores.

DETAILED DESCRIPTION

Embodiments of the present invention provide techniques for a visual disability detection system that employs virtual reality to assess visual performance of a patient based on activities of real life simulated in a virtual reality environment. A variety of daily activities can be simulated using virtual reality for measurement of visual disability. The daily activities simulated may include navigating on a busy street, walking up or down flights of stairs, driving a vehicle, and locating objects of interest in an environment such as objects on a shelf, etc. These activities of daily living are simulated because they are common scenarios in which patients with eye diseases or neurological disorders may encounter problems. For instance, patients with tunnel vision often experience difficulties navigating on a busy street with frequent bumping into objects or people despite the fact that they have relatively good central vision. Walking down a flight of stairs without risking fall or collision with oncoming people also poses a major concern for patients with inferior visual field loss. As the virtual reality testing environments are standardized, visual performance can be objectively quantified (e.g. time required to navigate through obstacles over a designated distance; number of collisions bumping into obstacles, etc.). This allows improved objective measurement, grading, and monitoring of visual disability.

Figure 1:
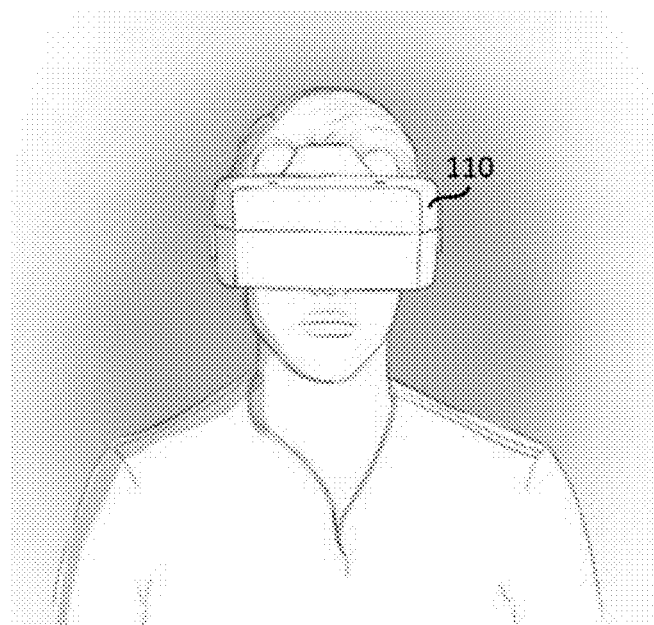
FIG. 1 illustrates a virtual reality platform, according to some embodiments.

FIG. 1 illustrates an example of a virtual reality platform that can be used in a visual disability detection system, according to some embodiments. The virtual reality platform may include a head-mounted display (HMD) unit 110 worn by a user as shown. HMD 110 can be used to project three-dimensional virtual reality (VR) environments with virtual objects for the user wearing HMD 110. In some embodiments, HMD 110 may include a headset with a display screen and one or more graphics converting units communicatively coupled to an external computing device (e.g., a computer, smartphone, tablet, gaming console, etc.) via a wired or wireless connection, and the VR environments can be sourced from the external computing device and projected onto the display screen of HMD 110. In some embodiments, HMD 110 may include a headset with a mount or a cradle configured to engage with the external device. The headset may include a connector that electrically connects the headset to the external device. The headset may contain additional batteries to extend the battery life of the mounted external device, and may include one or more powerful graphics processing units to enhance the graphical performance of the mounted external device. In some embodiments, HMD 110 can be an all-in-one headset integrated with one or more computing units (including processor, memory, etc.), one or more graphic processing units, batteries, and a display screen, and the VR environments can be generated by a program stored in the memory of HMD 110.

Figure 2:
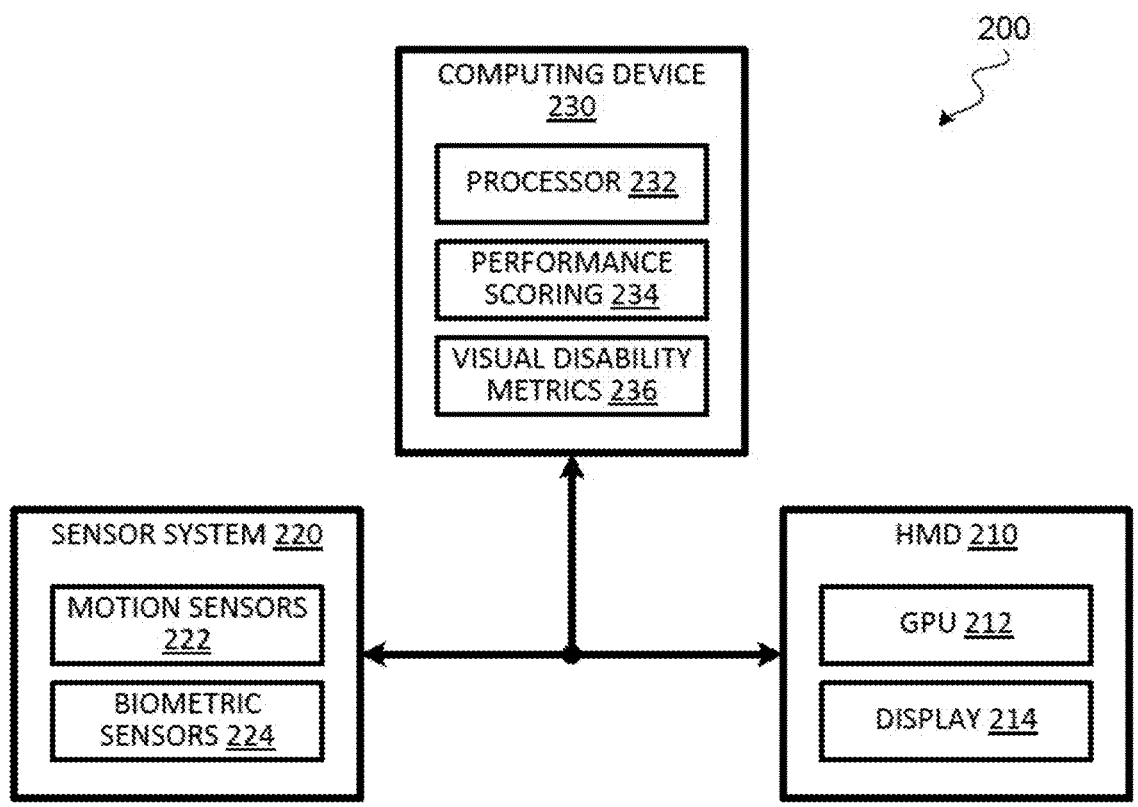
FIG. 2 illustrates a visual disability detection system, according to some embodiments.

FIG. 2 illustrates a block diagram of a visual disability detection system 200, according to some embodiments. Visual disability detection system 200 may include a head-mounted display (HMD) unit 210, a sensor system 220, and a computing device 230 communicatively coupled to each another. Although these components are illustrated as separate components in FIG. 2, it should be understood that some or all of the functionalities of any of the components can be integrated with another component in visual disability detection system 200.

HMD 210 can be a stereoscopic head-mounted display such as HMD 110, and may include one or more graphics processing units 212 or graphic converting units, and a display 214 that displays and renders virtual reality simulations in a virtual reality environment with virtual reality objects to simulate real life activities (e.g., activities of daily living of a person). The virtual reality simulations are used to test visual performance of the user wearing HMD 210 according to the responses of the user for measurement, grading, and monitoring of visual disability. HMD 210 coupling with sensor system 220 enables a user to interact with the projected VR environment, and to navigate through the virtual reality simulations. The virtual reality elements in the VR environment can be updated in real-time with reference to the user's responses during the virtual reality simulations.

In some embodiments, visual disability detection system 200 may include one or more input devices (e.g., keyboard, gamepad, mouse, pointer, etc.) communicatively coupled to the computing device 230 and HMD 210 to allow the user to control movement in the virtual reality simulations. HMD 210 may also include an audio output to provide instructions that guide and alert the user through the virtual reality simulations in the VR environment. The interaction between the user and the VR environment can also generate feedback to the user via output devices. For instance, a sound or a tactile vibration transmitted via a controller can be sent to the user signaling an event of collision with a virtual reality object in the VR environment.

As discussed above, in some embodiments, HMD 210 may have its own processing capabilities and storage memory such that the virtual simulations can be stored locally on HMD 210, or a program that generates the virtual simulations can be stored locally on HMD 210 and executed to create the virtual simulations. In some embodiments, the virtual simulations can be sourced from an external device (e.g., computing device 230), and the external device can optionally be mounted onto HMD 210. In such embodiments, HMD 210 may act as a slave display device, or HMD 210 may have its own graphics processing capabilities to enhance the graphics performance of the external device (e.g., to increase the resolution and/or frame rate to enhance the realism of the virtual reality simulations).

Examples of virtual reality simulations that can be generated and displayed on HMD 210 may include activities of daily living such as: (1) navigating in a busy street without bumping into other pedestrians; (2) walking up or down flights of stairs without bumping into obstacles; (3) driving a vehicle on a busy road from location A to location B; (4) locating an object of interest on a shelf, etc. In some embodiments, the virtual reality objects in the virtual reality simulations include one or more stationary objects in the VR environment such as stationary pillars or road barricades, and/or one or more dynamic objects that are moving in the virtual reality environment such as other pedestrians or other vehicles on a road. The contrast level of the virtual reality objects or brightness level of the virtual reality simulations can also be adjusted to simulate different lighting conditions. For example, vision of some users at night can be significantly impaired despite relatively normal vision at day time. The system is designed to evaluate and measure the performance of a user in completing daily tasks in different VR environments with different brightness and contrast levels, simulating activities of daily living in a variety of light conditions, thus allowing evaluation of the severity of visual disability at different levels of light intensity.

In some embodiments, the virtual reality simulations and the VR environment can also be adapted to simulate a real life environment that is specific to a particular user. For example, the user-specific real life environment of a particular user can be captured with a camera worn by the user as the user goes about his/her daily life, and a VR environment with the virtual objects resembling objects from the user-specific real life environment can be generated from the image data captured by the camera. By way of example, a video of a user going up and down a flight of stairs in the user's home can be captured, and a VR environment that mimics the stairs in the user's home (e.g., number of steps, step height, number of turns, etc.) can be generated for the virtual reality simulation. In this manner, the actual impact of the visual disability on a particular user can be accurately assessed based on the user's real life environment.

Sensor system 220 may include a number of sensors to monitor and record the user's voluntary responses (e.g., movement and motion) and involuntary responses (e.g., biometric readings) during the virtual reality simulations. In some embodiments, some or all of the sensors can be integrated into HMD 210, and/or some or all of the sensors can be placed on suitable parts of the body of the user. Sensor system 220 may include motion sensors 222 such as gyroscope, accelerometer, and/or magnetometer to sense the voluntary responses of the user. These responses may include, for example, orientation and movement of the head, the body trunk such as chest or waist, the eyeball, and the upper and lower limbs. In some embodiments, the movement detected by the motion sensors 222 can be used to control the movement in the virtual reality simulations. In some embodiments, the movement and orientation detected by the motion sensors 222 can be used separately to adjust the moving direction and the viewing direction in the virtual reality simulations. For example, a sensor attached on the waist of the user can be used as a reference for the moving direction in the virtual reality simulation, while a sensor embedded in the HMD 210 can be used as a reference for the viewing direction. The setting can increase the realistic feeling of the user and may reduce motion sickness. Sensor system 220 may also include biometric sensors to sense the involuntary responses of the user. Examples of such biometric sensors may include blood pressure sensor, heart rate sensor, optical sensor (e.g., infrared sensor) to detect oculomotor responses and changes in dilation or pupil size, and/or electroencephalogram (EEG) sensors to detect electrical brain activity. In some embodiments, if any input device is used by the user to control movement in the virtual reality simulations, the commands received via the input device can also be recorded, as well as any vocalization by the user reacting to the virtual reality simulations.

Computing device 230 (e.g., computer, smartphone, tablet, gaming console, etc.) may include one or more processors 232 and a memory storing program instructions to compute performance scores 234 and determine visual disability metrics 236 based on the voluntary and/or involuntary responses of the user to the virtual reality simulation and sensor readings from sensor system 220 relayed to computing device 230. In some embodiments, computing device 230 performing analysis on the user's visual disability can be the same device as the device from which the virtual simulations are sourced, or can be a different device such that the generation of the virtual reality simulations and analysis of visual disability are performed on separate devices. Parameters such as the time required in completing a task, the number of collisions with virtual reality objects in the VR environment (e.g., static obstacles such as pillar and road barricade, and moving obstacles such as other pedestrians and vehicles), the angle and the speed of collision, the brightness level in the virtual reality simulation, the contrast level of the virtual reality objects, the voluntary response tracking data, and/or involuntary response tracking data can be used by computing device 230 to calculate visual performance scores for the user. These performance scores can then be used to determine visual disability metrics of the user, and quantify the visual performance for assessment, grading, and monitoring of the visual disability. In some embodiments, the visual disability metrics determination process can take into account for the learning effect or the user. For example, the learning effect can be minimized by assigning the virtual reality objects at different locations when repeat testing in the same virtual reality environment is required. In some embodiments, the virtual reality testing environment can be standardized, and visual performance can be objectively quantified (e.g. time required to complete a task). This allows visual disability to be objectively assessed and its progression to be monitored over time. In some embodiments, the parameters of visual disability and the performance scores can be collected and uploaded to a database in a cloud server for real-time recording, calculating, reporting and monitoring of visual performance scores for visual disability assessment. The performance scores can be classified according to the user and the user's performance in the database. In some embodiments, deep learning and artificial intelligence can be used to improve the determination of the visual disability metrics. The performance scores can be displayed on a computing device such as a computer, a mobile computing device, or a smart phone, etc. The server can remotely send the results to the clinicians for monitoring the visual disability progression of the user. Clinicians or eye care providers can monitor the visual performance scores of the user remotely via internet access to the cloud server and devise any change of treatment approach accordingly.

Figure 3:
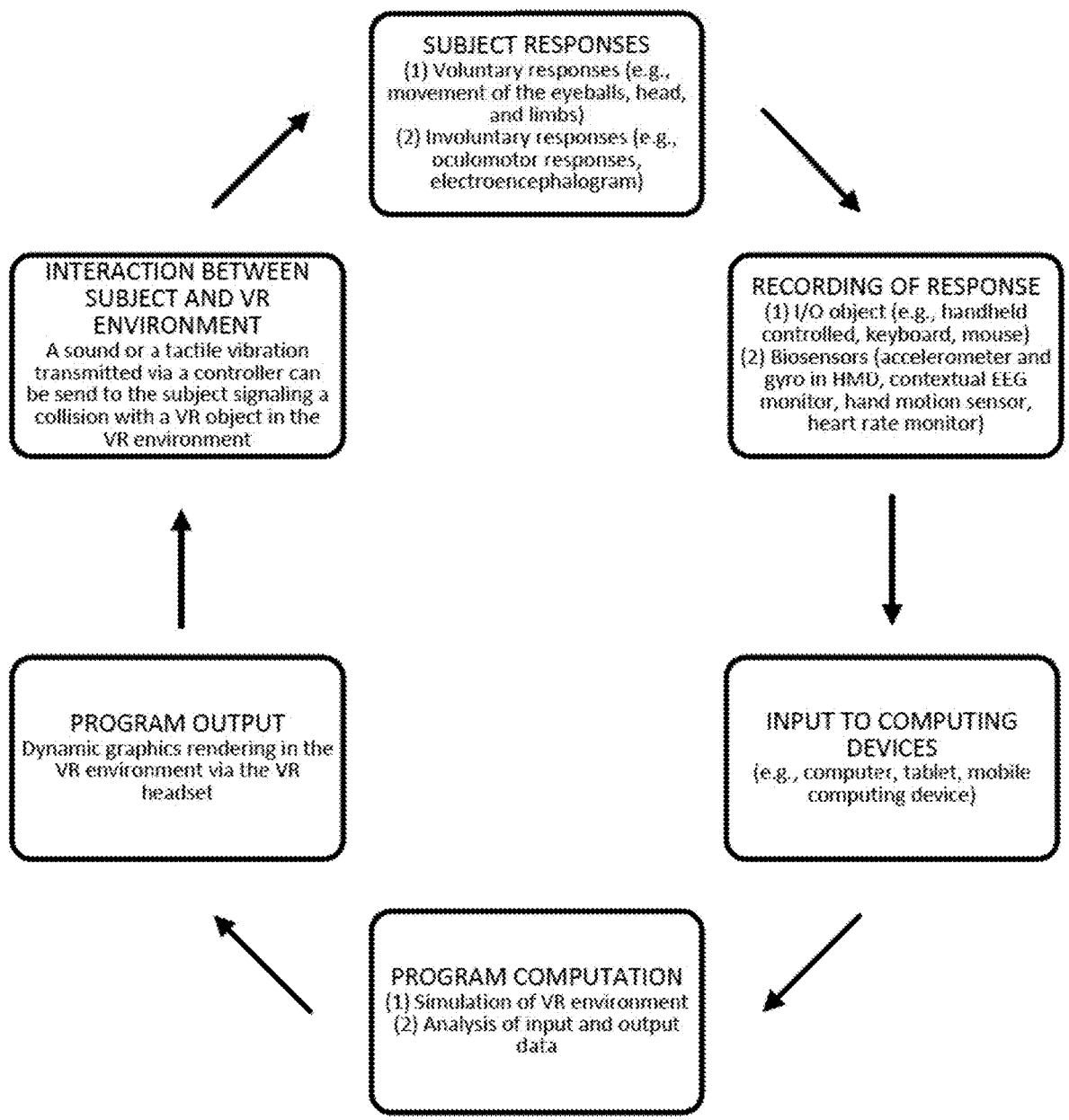
FIG. 3 illustrates an example workflow of an algorithm for measurement of visual disability, according to some embodiments.

FIG. 3 illustrates an example workflow of the algorithm for measurement of visual disability, according to some embodiments. VR elements are displayed in a stereoscopic head-mounted display and the user wearing the HDM is requested to follow an instruction to complete a task (e.g., navigating from location A to location B without bumping into obstacles or pedestrians, walking up or down flights of stair without bumping into obstacles or people, driving from location A to location B, locating objects of interest from a shelf, etc.). The instruction can be provided by audio or visual cues. In some embodiments, a practice of the control in the virtual reality simulations with standardized animations and audios as built-in instructions prior to the test can be included into the program. This can, for example, minimize the error in learning caused by insufficient instructions provided to the user from different technicians. Voluntary and involuntary responses of the user are recorded in response to the simulated VR environment. Voluntary responses may include, for example, movement of the head, the body, the eyeball, and the upper and lower limbs, and vocalization. Involuntary responses may include, for example, oculomotor responses, changes in pupil size, blood pressure, heart rate and electroencephalogram. The interaction with the VR environment can generate feedback via output devices. For instance, a sound or a tactile vibration transmitted via a controller can be sent to the user to signal a collision with a VR object in the VR environment. The user's responses are detected and monitored by input devices or monitoring sensors. The responses are relayed to a computing device or computing units of HMD. Parameters including the duration required for a user to complete a task, the number of stationary (e.g. pillar, road barricade) and moving obstacles (e.g. pedestrians, vehicles) that the subject collides with, the angle of collision and the speed of collision are measured to compute performance scores for measurement, grading and monitoring of visual disability.

Figure 4:
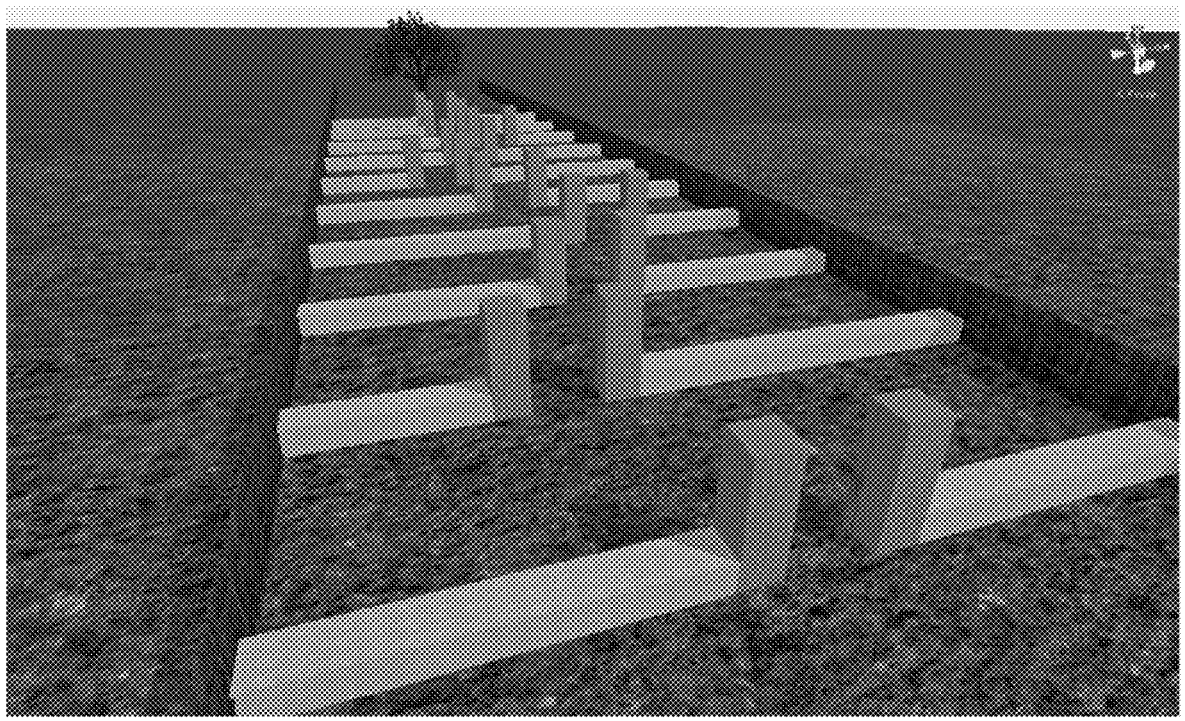
FIG. 4 illustrates an example of a virtual reality simulation in a virtual reality environment, according to some embodiments.
Figure 5:
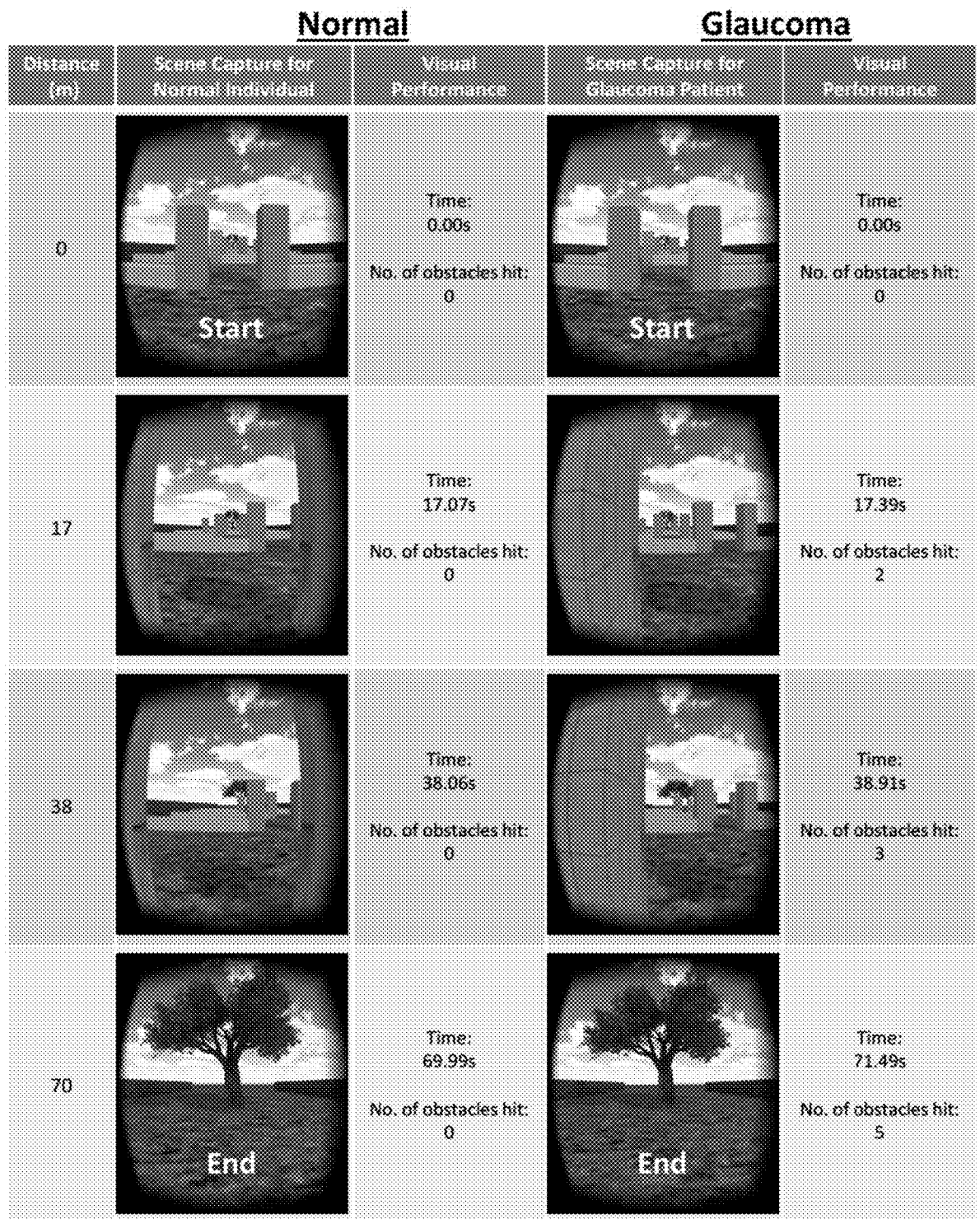
FIG. 5 illustrates serial screen captures from a virtual reality simulation in daylight for a normal subject and a glaucoma patient, according to some embodiments.
Figure 6:
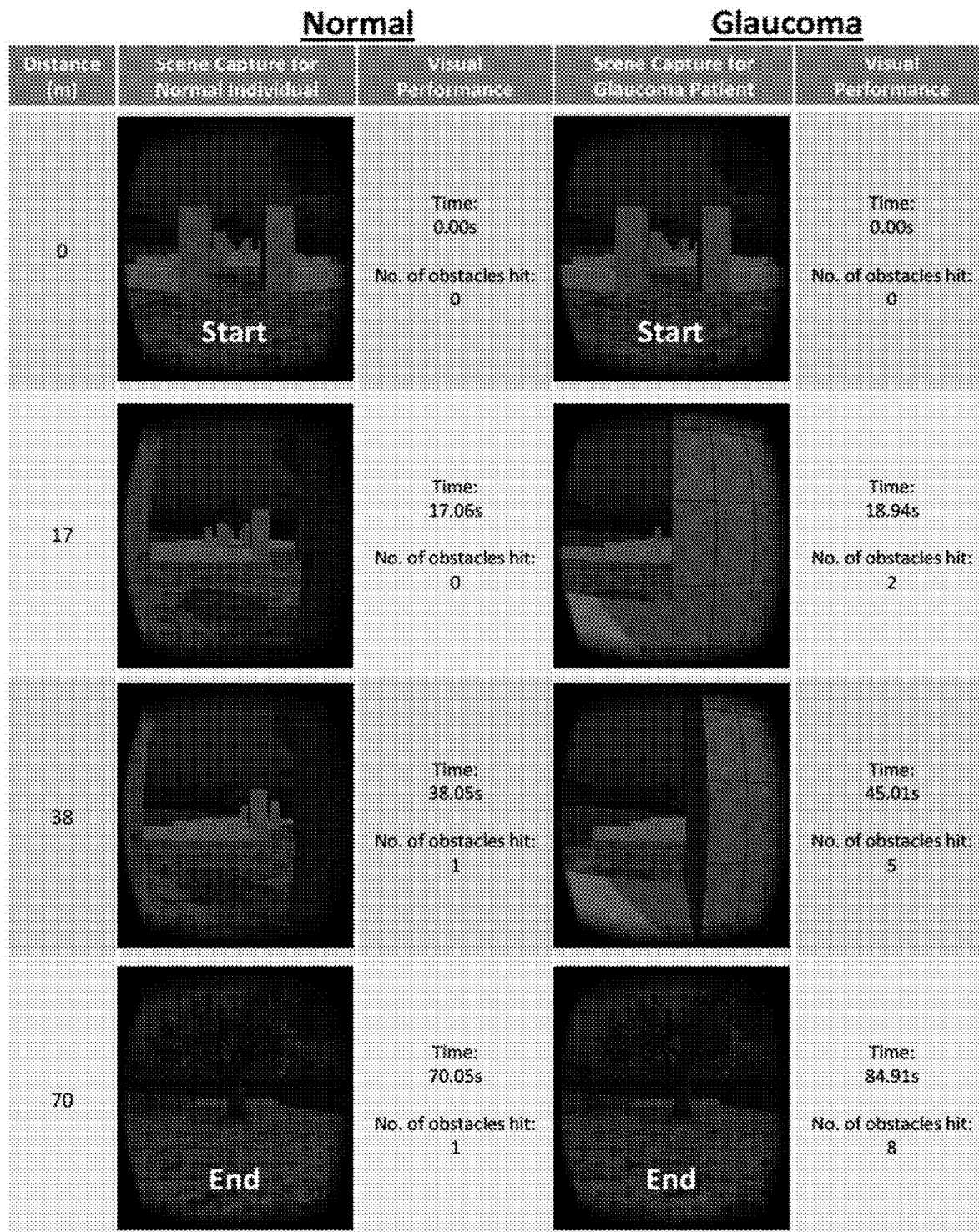
FIG. 6 illustrates serial screen captures from a virtual reality simulation at nighttime for a normal subject and a glaucoma patient, according to some embodiments.

FIG. 4 illustrates an example of a VR environment used to simulate a walk-through in a garden, according to some embodiments. In this example, the walk-through contains 10 barrier gates positioned at different locations over 70 meters long. Test subjects are requested to walk through the gates (2 meters in width) at a default speed (60 meters per minute) by turning the head and body to the right direction without bumping into the barriers. FIG. 5 shows serial screen captures from the virtual reality environment during daylight simulations for a normal subject and a glaucoma patient. The glaucoma patient with visual field abnormalities bumped into the virtual reality barriers 5 times during the test, whereas the normal subject completed the test in a shorter time without bumping into any virtual reality objects. A night-time virtual reality environment can also be generated. FIG. 6 illustrates serial screen captures from the virtual reality environment during nighttime simulations for a normal subject and a glaucoma patient. Of note, the performance of the glaucoma patient was much worse at night, in terms of the time required to complete the test and the number of barriers hit during the test as compared with the normal subject. This example demonstrates that the use of virtual reality simulations is capable of conducting clinical testing in patients with visual impairment.

Additional examples of virtual reality simulations are described in more details below. In any of the VR environments, because visual performance and visual disability may vary with the lighting conditions of the environment, the virtual reality simulation can be administered in different brightness and contrast levels, simulating different lighting conditions.

Example 1—Navigation in a Busy City Area

In some embodiments, a busy city area in which stationary (e.g. street light pole, trash bin) and dynamic (e.g. pedestrians, vehicles) objects are simulated. The subject is asked to navigate from location A to location B without bumping into any objects or persons in the VR environment. Head and/or body motion data are measured and monitored in real-time during VR simulation with motion sensors in the HMD. The subject navigates in the VR environment by changing head and/or body orientation and the navigation speed can be adjusted with a controller in hand or a motion detector of the lower limbs. The subject directly interacts with the VR environment and the VR graphics change in response to the subject's responses. The program can generate an alert in the form of visual and/or audio cues to the subject when a collision with the VR objects occurs. The program detects and measures the number of collisions, the angle and the speed of collision between the subject and VR objects, the size, color and/or contrast of the collided VR objects, and records the duration required to complete the navigation for computation of performance scores to measure, grade and monitor visual disability.

Similar navigation performance tasks can be administered in customized VR environments (garden, department store, supermarket, etc.) to simulate the activities of daily living of a specific person using similar parameters (i.e. the duration required to complete the journey, the number of collisions, the angle and the speed of collision, etc.) to measure visual disability.

Example 2—Walking Up or Down Flights of Stairs

In some embodiments, the subject is asked to walk up and down several flights of stairs without bumping into obstacles or people along the path. Head and/or body motion data are measured and monitored in real-time during VR simulation with motion sensors in the HMD. The subject navigates in the VR environment by changing head and/or body orientation and the navigation speed can be adjusted with a controller or a motion detector of the lower limbs. The subject directly interacts with the VR environment and the VR graphics change in response to the subject's responses. The program can generate an alert in the form of visual and/or audio cues to the subject when a collision with the VR objects occurs. The program detects and measures the number of collisions, the angle and the speed of collision between the subject and VR objects, the moving direction (upward, forward or downward) of the subject in the VR environment, the size, color and/or contrast of the collided VR objects, and records the duration required to complete the navigation for computation of performance scores to measure, grade and monitor visual disability.

Example 3—Driving

In some embodiments, the program provides a driving simulation including stationary (e.g. roadblocks, lampposts, trees, cars on the road side, etc.) and dynamic (e.g. vehicles, pedestrians crossing the road, highway maintenance workers, stray and wandering animals, etc.) objects in the VR environment. The VR environment can be simulated in different traffic and weather conditions (e.g. highway, city traffic, uphill, downhill, heavy rain, etc.). The subject is required to drive from location A to location B without colliding with any objects in the VR environment. Head and/or body motion data are measured and monitored in real-time during VR simulation with motion sensors in the HMD. The subject can turn a wheel controller to change the direction of navigation and the navigation speed can be changed with an accelerator and a brake controller. The subject directly interacts with the VR environment and the VR graphics change in response to the subject's responses. The program will generate an alert in the form of visual and/or audio cues to the subject when a collision with the VR objects occurs. The program detects and measures the number of collisions, the angle and the speed of collision between the subject and VR objects, the size, color and/or contrast of the collided VR objects, and records the duration required to complete the navigation for computation of performance scores to measure, grade and monitor visual disability.

Example 4—Locating Objects of Interest

In some embodiments, the subject is required to locate objects of interest (e.g. a book, a bottle, a pin, etc.) from a shelf or a container containing mixtures of objects. Head and/or body motion data are measured and monitored in real-time during VR simulation with motion sensors in the HMD. The subject uses a controller or hand and body gestures detected by motion sensors to locate the targeted object. The subject directly interacts with the VR environment and the VR graphics would change in response to the subject's responses. The duration required to complete the task and the number of correctly located items are used to generate a visual performance score for measurement of visual disability.

Figure 7:
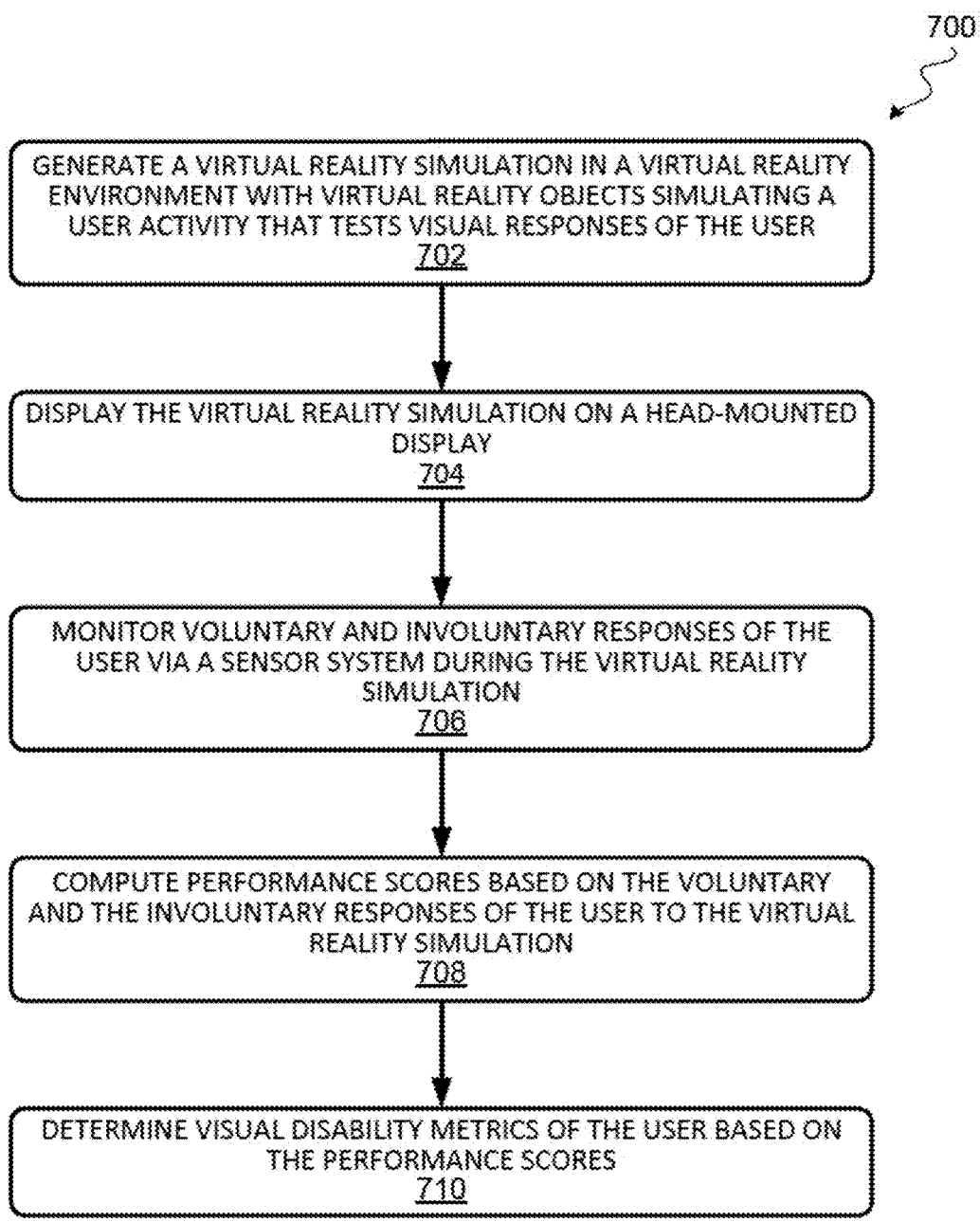
FIG. 7 illustrates a flow diagram of a process for detecting and measuring visual disability, according to some embodiments.

FIG. 7 illustrates a flow diagram of a process 700 for detecting and measuring visual disability, according to some embodiments. In some embodiments, process 700 can be implemented as computer readable code as part of a computer program, and can be embodiment in a non-transitory computer readable medium.

At block 702, a virtual reality simulation in a virtual reality environment with virtual reality objects is generated. The virtual reality simulation can simulate a user activity that tests visual responses of the user. The virtual reality simulation can be, for example, navigating in a busy city area, walking up or down one or more flights of stairs, driving a vehicle, and locating one or more objects of interest, etc.

At block 704, virtual reality simulation is displayed on a head-mounted display. In some embodiments, at least one of a contrast level or a brightness level of the virtual reality simulation being displayed on the head-mounted display can be adjusted to simulate different lighting conditions.

At block 706, voluntary and involuntary responses of the user can be monitored and recorded via a sensor system during the virtual reality simulation. For example, motion sensors can be used to sense one or more of eye motion, head motion, limb motion, or body motion of the user, etc.; and biometric sensors can be used to sense one or more of blood pressure, heart rate, eye dilation, or electrical brain activity, etc.

At block 708, performance scores based on the voluntary and the involuntary responses of the user to the virtual reality simulation can be computed. At block 710, visual disability metrics can be determined based on the performance scores. In some embodiments, the visual disability metrics can be determined based on one or more measurements recorded from the virtual reality simulation, for example, duration required to complete a task in the virtual reality simulation, number of collisions with virtual reality objects in the virtual reality simulation, angle and/or speed of collisions with virtual reality objects in the virtual reality simulation, size, color and/or contrast of VR objects related to the event, and/or number of correctly located objects of interest in the virtual reality simulation.

In some embodiments, the visual disability metrics can be determined by developing a multivariate statistical analysis model integrating combinations of different performance scores, for example, by taking the number of collision events in the virtual reality simulations into account when calculating the correlation between the time duration to complete a task and the measured visual field index of a user. In some embodiments, the visual disability metrics can be determined using techniques involving artificial intelligence such as deep learning or machine learning.

In some embodiments, the visual performance data of a user evaluated with VR simulation in a clinic or in a remote location (e.g. home, office) can be stored on the VR computing device or uploaded to a remote server. These data can then be processed for the purposes of recording, calculating, reporting, and monitoring of visual performance scores. Patients and/or their care providers can measure and monitor their visual performance scores remotely via internet access.

In some embodiments, the surrounding environment in the real world can be captured by one or more cameras of the HMD and projected onto the HMD in real-time, similar to the live preview on the screen of a digital camera, but the projected scene in HMD can be three-dimensional. Prior to projecting onto the HMD, the captured environment can also be analyzed in real-time according to the tested visual performance and visual disability metrics stored in the database for prediction of objects that may not be noticed by the user. The brightness and/or contrast levels of the captured environment can be modified to augment the visibility of the real-life environment. VR objects can be added and projected to the captured real-life environment to provide visual aids to the user. This can, for example, assist a user going up or down a flight of stairs at home or in a subway station by amplifying the brightness of the staircase and increasing the contrast of the objects on the staircase. The user can also be alerted with a virtual visual aid before colliding with a nearby object.

Thus, a user's vision can be improved by using the visual disability metrics determined by the visual disability detection system. The vision improving techniques may include capturing the real life environment with a camera attached to the user or on the head-mounted display, and predicting undetectable real life objects that the user's vision is unable to detect due to the vision loss according to the measured visual disability of the user. The depth of the real life objects can be captured with a depth camera to enhance the accuracy for the prediction of the undetectable real life objects according to the visual disability of the user. An augmented reality environment which resembles the captured real life environment can be generated with additional virtual reality objects displayed on top as a hint for helping the user to detect the real life objects. In some embodiments, the brightness level of the captured real life environment and the contrast level of the captured real life objects can be modified according to the prediction of the undetectable real life objects, and the augmented reality environment which resembles the captured real life environment can be generated with the modified brightness and contrast to aid the user's vision.

Accordingly, techniques employing virtual reality in a visual disability detection system has been described. The application of virtual reality has been largely limited to the gaming industry. Virtual reality as a platform for clinical evaluation of visual disability has not been examined until now. There has been no past commercially available tools for clinical measurement of visual disability related to activities of daily living. The techniques of generating virtual reality environments for evaluation of visual disability can impact clinical management of a variety of eye diseases and neurological disorder affecting the visual pathway. Specifically, visual performance measurement related to patients' activities of daily living would provide a more direct and clinically relevant indicator reflecting visual disability and its impact on quality of life compared with the existing clinical parameters like visual acuity and visual field measures. Being able to simulate daily tasks for evaluation of visual performance, clinicians can better understand from a patient's perspective how visual impairment impacts daily tasks. The techniques described herein can empower clinicians to devise appropriate treatment, support and visual aids to improve patients' quality of vision and quality of life. Unlike many clinical instruments for testing of vision, the virtual reality platform is also portable. Home monitoring of vision and visual performance is therefore feasible. Some chronic eye diseases, like glaucoma (a leading cause of irreversible blindness) are characterized by progressive worsening and constriction of visual field with relatively well preserved central vision until the end stages. Regular monitoring of visual field every 3-4 months has been recommended for management of glaucoma patients as disease progression can occur without noticeable symptoms. The virtual reality platform for home monitoring of visual performance as described herein not only can facilitate early detection of disease progression (which may necessitate treatment augmentation), but can also decrease the cost of frequent clinic visits for visual field testing incurred to patients and health care providers.

Additional examples of virtual reality simulations are shown in FIGS. 8A to 11. In some embodiments, the virtual reality simulations simulate daily activities in real life, including: (i) identifying and selecting objects from a supermarket rack; (ii) walking up and down flights of stairs; and (iii) navigating in a city area packed with pedestrians and vehicles.

Figure 8A:
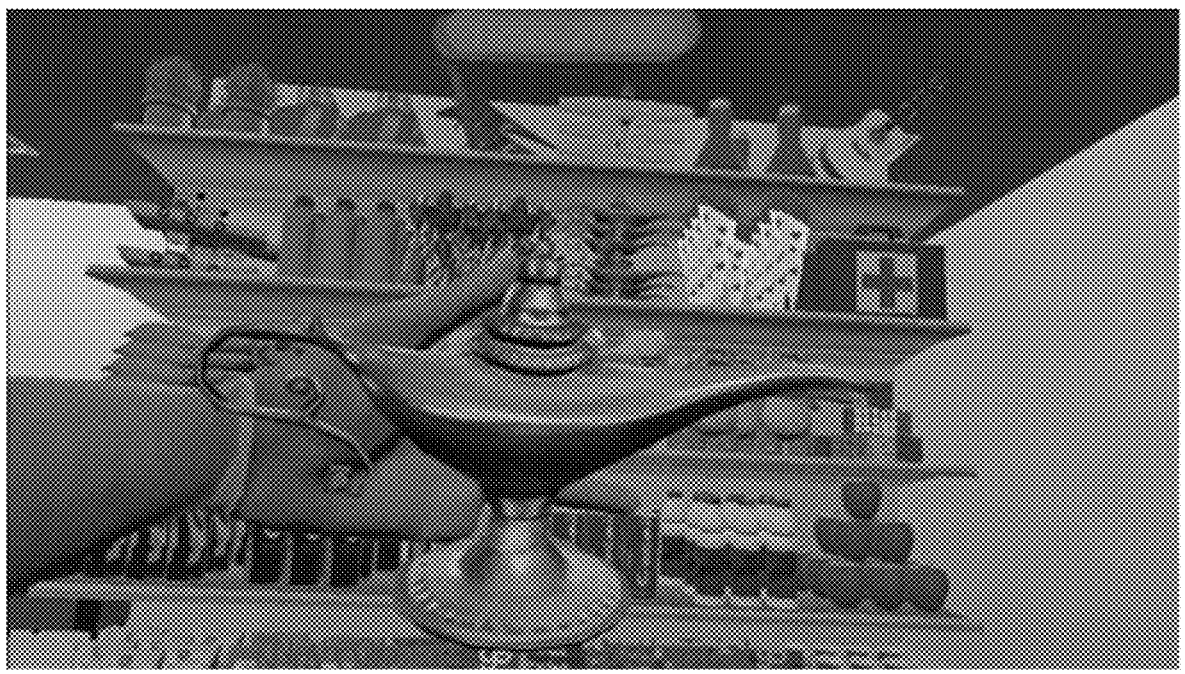
FIG. 8A illustrates a virtual reality simulation of identifying and selecting objects from a supermarket rack, according to some embodiments.
Figure 8B:
FIG. 8B illustrates another virtual reality simulation of identifying and selecting objects from a supermarket rack, according to some embodiments.
Figure 9A:
FIG. 9A illustrates a virtual reality simulation of walking up and down flights of stairs, according to some embodiments.
Figure 9B:
FIG. 9B illustrates another virtual reality simulation of walking up and down flights of stairs, according to some embodiments.
Figure 10A:
FIG. 10A illustrates a virtual reality simulation of navigating in a city area packed with pedestrians and vehicles, according to some embodiments.
Figure 10B:
FIG. 10B illustrates another virtual reality simulation of navigating in a city area packed with pedestrians and vehicles, according to some embodiments.
Figure 10C:
FIG. 10C illustrates a further virtual reality simulation of navigating in a city area packed with pedestrians and vehicles, according to some embodiments.

FIGS. 8A & 8B illustrate a tested subject first identifying a target object to be found from a supermarket rack and then choose the target object from the supermarket rack in a VR simulation. FIGS. 9A & 9B illustrate a tested subject walking up and down several flights of stairs in a VR simulation while being required to avoid collisions with any obstacles on the way to the destination. FIGS. 10A, 10B & 10C illustrate a tested subject navigating in a city area packed with pedestrians and vehicles while being required to avoid bumping into obstacles, other pedestrians and cross a road without being hit by the vehicles in the traffic.

Figure 11:
FIG. 11 illustrates a virtual reality simulation of navigating in a city area packed with pedestrians and vehicles in a dark night, according to some embodiments.

In some embodiments, the user is tested in different light intensity levels for the same daily activity simulation. FIG. 11 illustrate a tested subject navigating in a city area similar to the simulation setting in FIGS. 10A, 10B & 10C while the light intensity of the VR environment is changed to a dark light.

In some embodiments, the collected data is analyzed to compute performance scores. In some embodiments, the collected data is further combined to perform multivariate statistical analysis and/or a cluster analysis for determining the visual disability metrics of the tested subject.

Any of the computing devices, computers, servers, and the like described herein can be implemented using one or more processors coupled to a memory that store code or instructions, which when executed by the one or more processors, cause the device to perform one or more of the methods and processes described herein. Memory, storage media, and computer-readable media for containing code, or portions of code described herein, can include any appropriate media known or used in the art, including storage media and communication media, such as but not limited to volatile and non-volatile, removable and non-removable media implemented in any method or technology for storage and/or transmission of information such as computer-readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, data signals, data transmissions, or any other medium which can be used to store or transmit the desired information and which can be accessed by the computer. Based on the disclosure and teachings provided herein, a person of ordinary skill in the art will appreciate other ways and/or methods to implement the various embodiments.

The above description is illustrative and is not restrictive. Many variations of the various embodiments may become apparent to those skilled in the art upon review of the disclosure. The scope of the invention may, therefore, be determined not with reference to the above description, but instead may be determined with reference to the pending claims along with their full scope or equivalents.

The methods and processes described herein are exemplary in nature, and the methods and processes in accordance with some embodiments may perform one or more of the steps in a different order than those described herein, include one or more additional steps not specially described, omit one or more steps, combine one or more steps into a single step, split up one or more steps into multiple steps, and/or any combination thereof.

It may be understood that some embodiments as described above can be implemented in the form of control logic using computer software in a modular or integrated manner. Based on the disclosure and teachings provided herein, a person of ordinary skill in the art may know and appreciate other ways and/or methods to implement the present invention using hardware and a combination of hardware and software.

Any of the software components or functions described in this application, may be implemented as software code to be executed by a processor using any suitable computer language such as, for example, Java, C++, C #, Python or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

One or more features from any embodiment may be combined with one or more features of any other embodiment without departing from the scope of the invention.

A recitation of "a," "an," or "the" is intended to mean "one or more" unless specifically indicated to the contrary.

What is claimed is:

1. A visual disability detection method implemented by computer, or a processor executing non-transitory computer readable storage medium comprising code, the method including the steps of:
   generating a virtual reality simulation in a virtual reality environment with virtual reality objects, wherein the virtual reality simulation simulates a real life activity that tests visual responses of the user;
   displaying the virtual reality simulation on a head-mounted display;
   instructing the user to perform a task with a video and audio interface;
   adjusting of a brightness level of the virtual reality simulation and a contrast level of the virtual reality environment being displayed on the head-mounted display to simulate different lighting conditions;
   monitoring voluntary and involuntary responses of the user via a sensor system during the virtual reality simulation;
   computing performance scores based on the voluntary and the involuntary responses of the user to the virtual reality simulation, wherein the performance scores are computed over the different lighting conditions; and
   determining visual disability metrics of the user based on the performance scores.

2. The visual disability detection method of claim 1, wherein the real life activity being simulated includes at least one of navigating in a city area, walking up or down one or more flights of stairs, driving a vehicle, or locating one or more objects of interest from a shelf.

3. The visual disability detection method of claim 1, wherein the virtual reality objects include one or more stationary objects, or one or more dynamic objects that are moving.

4. The visual disability detection method of claim 1, wherein the sensor system includes motion sensors to sense the voluntary responses of the user, and biometric sensors to sense the involuntary responses of the user.

5. The visual disability detection method of claim 4, wherein the voluntary responses include eye motion, head motion, limb motion, or body motion of the user.

6. The visual disability detection method of claim 4, wherein the involuntary responses include blood pressure, heart rate, eye dilation, or electrical brain activity of the user.

7. The visual disability detection method of claim 1, wherein the sensor system detects head orientation and body trunk orientation separately to adjust viewing direction and moving direction respectively in the virtual reality environment to reduce motion sickness.

8. The visual disability detection method of claim 1, wherein the performance scores are computed based on at least one of the following parameters: a duration required to complete a task in the virtual reality simulation, a number of collisions with virtual reality objects in the virtual reality simulation, angle and speed of each collision with virtual reality objects in the virtual reality simulation, a number of correctly located objects of interest in the virtual reality simulation, brightness level in the virtual reality simulation, size, color, and contrast levels of the collided virtual reality objects, voluntary response tracking data, or involuntary response tracking data.

9. The visual disability detection method of claim 1, wherein the visual disability metrics determination process minimizes a learning effect by assigning the virtual reality objects at different locations when repeat testing in the same virtual reality environment is required.

10. The visual disability detection of claim 1, wherein the visual disability metrics are determined with a multivariable statistical analysis involving combinations of the performance scores.

11. The visual disability detection method of claim 1, further comprising steps of:
uploading parameters of visual disability and the performance scores to a server;
classifying the user and the user's performance into a database; and
displaying the performance scores on a computer or a mobile computing device or a smart phone.

12. The visual disability detection method of claim 11, wherein the server remotely sends the results to clinicians for monitoring visual disability progression of the user.

13. A visual disability detection method implemented by computer, or a processor executing non-transitory computer readable storage medium comprising code, the method including the steps of:

generating a virtual reality simulation in a virtual reality environment with virtual reality objects, wherein the virtual reality simulation simulates a real life activity that tests visual responses of the user;
displaying the virtual reality simulation on a head-mounted display;
instructing the user to perform a task with a video and audio interface;
monitoring voluntary and involuntary responses of the user via a sensor system during the virtual reality simulation;
computing performance scores based on the voluntary and the involuntary responses of the user to the virtual reality simulation;
determining visual disability metrics of the user based on the performance scores;
uploading parameters of visual disability and the performance scores to a server;
classifying the user and the user's performance into a database; and
displaying the performance scores on a computer or a mobile computing device or a smart phone.

14. The visual disability detection method of claim 13, wherein the server remotely sends the results to clinicians for monitoring visual disability progression of the user.

15. The visual disability detection method of claim 13, wherein the performance scores are computed based on at least one of the following parameters: a duration required to complete a task in the virtual reality simulation, a number of collisions with virtual reality objects in the virtual reality simulation, angle and speed of each collision with virtual reality objects in the virtual reality simulation, a number of correctly located objects of interest in the virtual reality simulation, brightness level in the virtual reality simulation, size, color, and contrast levels of the collided virtual reality objects, voluntary response tracking data, or involuntary response tracking data.

16. The visual disability detection method of claim 13, wherein the visual disability metrics determination process minimizes a learning effect by assigning the virtual reality objects at different locations when repeat testing in the same virtual reality environment is required.

* * * * *